United States Patent [19]

Rechmeier et al.

[11] 4,257,850
[45] Mar. 24, 1981

[54] PURIFICATION OF 1,2-DICHLOROETHANE RECOVERED IN THE INCOMPLETE THERMAL CRACKING TO VINYL CHLORIDE

[75] Inventors: Gerhard Rechmeier, Erftstadt; Ulrich Roesnik, Hürth; Harald Scholz, Erftstadt, all of Fed. Rep. of Germany

[73] Assignee: Hoechst Aktiengesellschaft, Fed. Rep. of Germany

[21] Appl. No.: 115,205

[22] Filed: Jan. 25, 1980

[30] Foreign Application Priority Data

Jan. 31, 1979 [DE] Fed. Rep. of Germany ....... 2903640

[51] Int. Cl.³ ............................................. B01D 3/34
[52] U.S. Cl. ...................................... 203/29; 203/75; 203/78; 570/262
[58] Field of Search .............. 260/652 P, 660, 656 R; 203/29, 78, 75

[56] References Cited
U.S. PATENT DOCUMENTS

| | | | |
|---|---|---|---|
| 3,876,714 | 4/1975 | Coppens | 260/656 R |
| 4,060,460 | 11/1977 | Smalley et al. | 260/652 P |

Primary Examiner—Delbert E. Gantz
Assistant Examiner—Joseph A. Boska
Attorney, Agent, or Firm—Connolly and Hutz

[57] ABSTRACT

Figure 2:
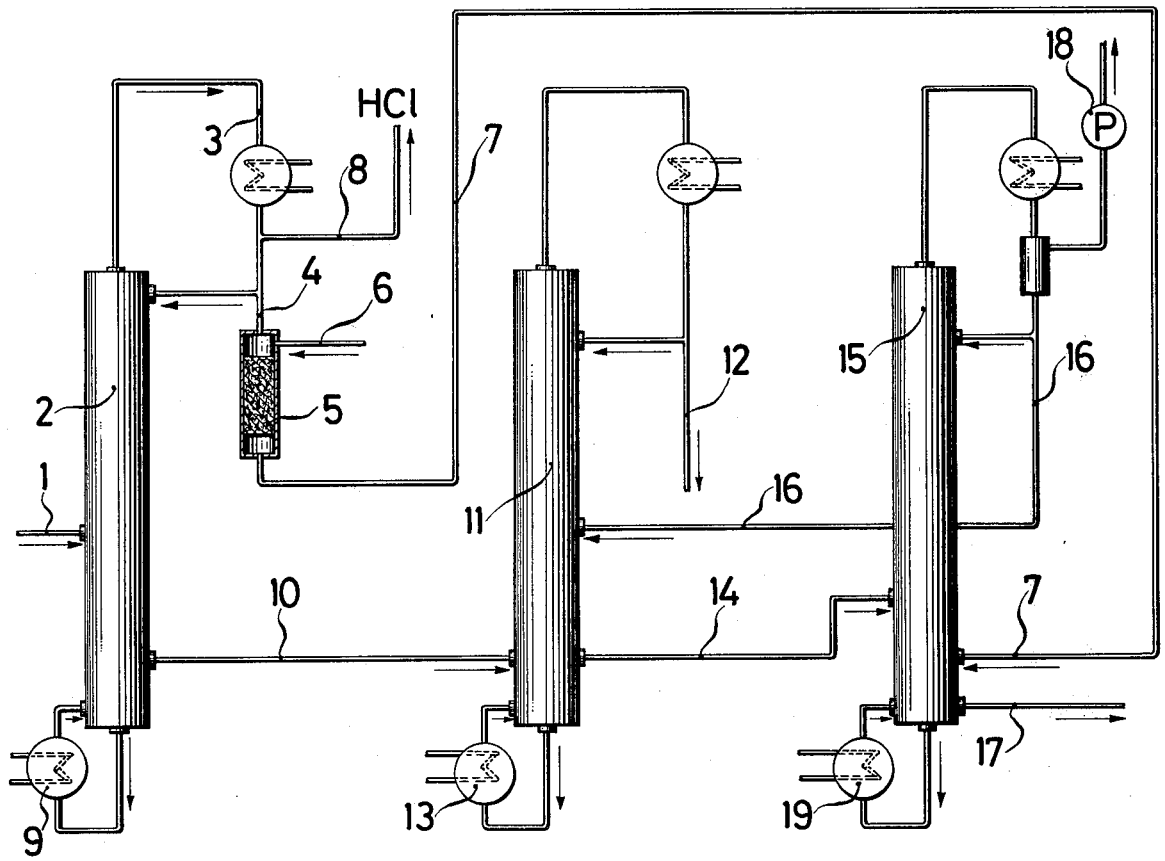

The invention relates to a process for purifying 1,2-dichloroethane which is recovered during incomplete thermal cracking to vinyl chloride and contains contaminants boiling at a temperature lower than 83.7° C. under a pressure of 1011 millibars, briefly termed low boilers, and contaminants boiling at a temperature higher than 83.7° C. under a pressure of 1011 millibars, briefly termed high boilers. More particularly, low boilers are distilled off overhead from contaminated 1,2-dichloroethane, in a first distilling zone; a portion of low boiler concentrate is continuously treated at 30° to 85° C. with gaseous chlorine and converted to high boilers; pure 1,2-dichloroethane is distilled off overhead from high boilers, in a second distilling zone; and residual dichloroethane is distilled off under reduced pressure from high boiler concentrate, in a third distilling zone, and the high boilers are removed; high boiler-containing effluent coming from the chlorination of low boiler concentrate is introduced into the lower portion of the third distilling zone (FIG. 2 of accompanying drawing).

2 Claims, 3 Drawing Figures

PURIFICATION OF 1,2-DICHLOROETHANE RECOVERED IN THE INCOMPLETE THERMAL CRACKING TO VINYL CHLORIDE

It has already been described (cf. German Pat. Nos. 857,957 and 899,191; U.S. Pat. No. 2,724,006 and British Pat. No. 938,824) that vinyl chloride can be produced by subjecting 1,2-dichloroethane to incomplete thermal cracking. A proportion, generally 40 to 60%, of 1,2-dichloroethane remains unconverted during that thermal reaction, for which it is necessary to be freed from contaminants prior to recycling it to the cracking unit. In order to avoid adverse effects on the service life of the heating coil forming part of the cracking reactor, it is invariably necessary for the 1,2-dichloroethane to be very carefully freed from its contaminants which, even if present in minor concentration, commonly undergo decomposition to carbon which is liable to deposit in the heating coil of the cracking (pyrolyzing) reactor and apparatus components disposed downstream thereof. As a result, it is necessary for these structural parts to be cleaned with additional expenditure, loss of desirable product and adverse effects on production capacity.

Figure 1:
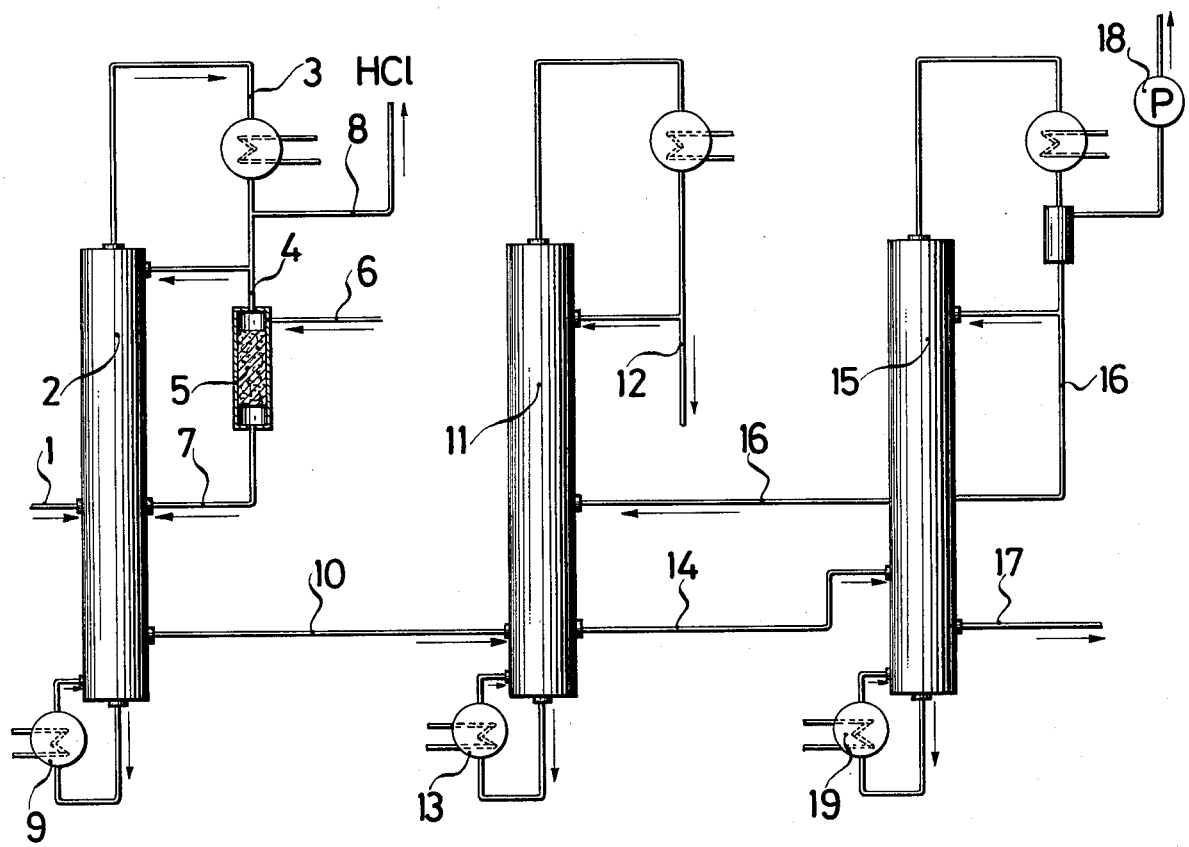

In U.S. Pat. No. 2,748,176 and German Pat. No. 1,917,933, it has been suggested that recovered 1,2-dichloroethane should be chlorinated so as to effect conversion of its low boiling contaminants to high boiling contaminants, for example by a process such as described hereinafter with reference to the accompanying flow scheme (FIG. 1).

1,2-dichloroethane which is free from hydrogen chloride and vinyl chloride but still contains contaminants boiling at a temperature lower than 83.7° C. under a pressure of 1011 millibars (termed low boilers hereinafter) and contaminants boiling at a temperature higher than 83.7° C. under a pressure of 1011 millibars (termed high boilers hereinafter) is recovered from the cracking stage and delivered through a conduit (1) to the center portion of a low boiler column (2) which is operated under atmospheric pressure and in which the low boilers are distilled off overhead through a conduit (3), condensed and partially recycled to the head of column (2). A partial stream (4) of condensed low boilers is introduced into a container (5) which is packed with iron and supplied with gaseous chlorine coming through a conduit (6). Inside container (5), the low boilers are chlorinated to high boilers at 30–85° C. in contact with an iron chloride catalyst originating from iron and chlorine. Effluent matter (7) coming from the chlorination container (5) is recycled approximately to the center portion of column (2). Hydrogen chloride which is evolved during the chlorination is allowed to escape through a conduit 8 downstream of the condenser. Column (2) is heated by means of a circulation evaporator (9). Product accumulating in the base portion of low boiler column (2) is delivered through a conduit (10) to high boiler column (11), which is operated under atmospheric pressure and in which pure 1,2-dichloroethane is distilled off overhead, condensed and removed through a conduit (12). Column (11) is heated by means of a circulation evaporator (13). Product accumulating in the base portion of high boiler column (11) is introduced through a conduit (14) into a column (15) which is operated under vacuum and in which residual 1,2-dichloroethane is distilled off, condensed and recycled through a conduit (16) to high boiler column (11). High boilers accumulating in the base portion of column (15) are removed discontinuously through conduit (17), and incinerated. The vacuum prevailing in column (15) is produced with the aid of a vacuum pump (18). Column (15) is heatable by means of a circulation evaporator (19). This is the prior art process described in Example 1 hereinafter which however is not fully satisfactory inasmuch as column (2) is liable to become blocked and in the end clogged by solid matter which is formed during the chlorination in container (5) and which consists essentially of iron chloride with some minor proportion of carbon. This naturally has adverse effects on the service life of the column (2) and circulation evaporator (9) which indeed can be operated for a relatively short while only. Needless to say also that the process takes place under irregular conditions whenever the above structural components become blocked or clogged, and low boiling contaminants may then actually find their way into the high boiler column (11) through conduit (10), and into the cracking zone, through head conduit (12).

In accordance with our present invention, we have unexpectedly found that column (2) is substantially not liable to become blocked if the outlet (7) of the chlorination container (5) is arranged so as to open into the lower portion of vacuum column (15). This is shown in the accompanying flow scheme, FIG. 2 which except for this arrangement of the outlet (7) is identical with FIG. 1. In the apparatus so modified, it is possible for solid contaminants to be removed continuously from the vacuum column (15) through conduit (17). This has technically beneficial effects on the service life of the low boiler column (2) which can be operated over prolonged periods of time, and on the quality of 1,2-dichloroethane which is taken from the high boiler column (11) through outlet (12). This process is described in Example 2 hereinafter.

Outlet (16) of vacuum column (15), which should preferably be operated under a pressure of 200 to 400 millibars and at a temperature of 75° to 95° C. in the column base portion, is however liable to become soiled with hydrogen chloride that originates from high boilers undergoing some minor cracking during distillation under vacuum. In addition to this, a portion of hydrogen chloride originating from the low boiler chlorination in container (5) may flow into vacuum column (15) through conduit (7) (FIG. 2) rather than to escape through off-gas line (8). As results from FIGS. 1 and 2, it is possible for contaminated 1,2-dichloroethane travelling through conduit (16) to flow back into high boiler column (11), and it is possible for low boilers (boiling at a temperature lower than 83.7° C. under a pressure of 1011 millibars) to get into the cracking zone, through conduit (12).

Figure 3:
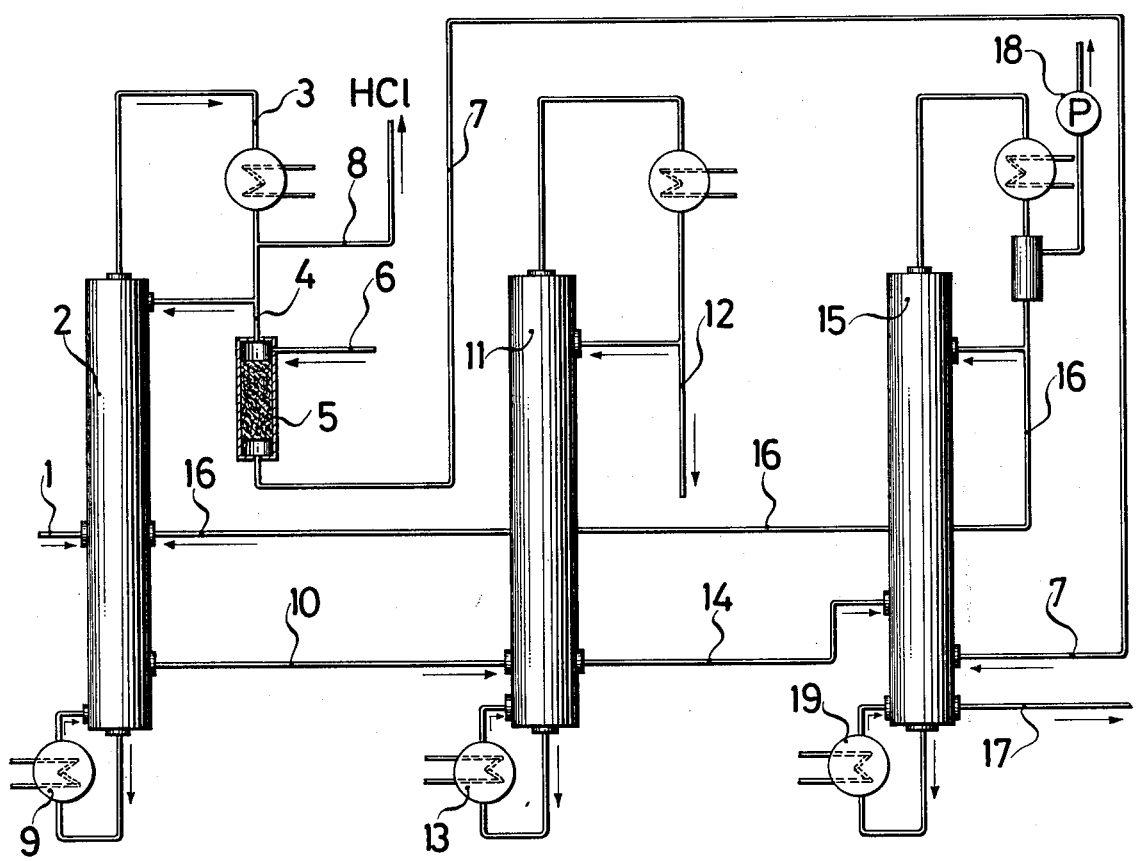

To avoid this adverse effect, the invention provides for the outlet (16) to be arranged so as to run back to, and open approximately into, the center portion of the low boiler column (2) inside which the low boilers are chlorinated to high boilers; this is shown in the accompanying flow scheme, FIG. 3 which except for this arrangement of outlet (16) is identical with FIG. 2. The process involving this additional step is described in Example 3 hereinafter. The present invention relates more particularly to a process for purifying 1,2-dichloroethane which is recovered during incomplete thermal cracking to vinyl chloride and contains contaminants boiling at a temperature lower than 83.7° C. under a pressure of 1011 millibars, briefly termed low boilers hereinafter, and contaminants boiling at a temperature higher than 83.7° C. under a pressure of 1011 millibars, briefly termed high boilers hereinafter, wherein the low boilers are distilled off overhead from contaminated 1,2-dichloroethane, in a first distilling zone; a portion of low boiler concentrate is continuously treated at 30° to 85° C. with gaseous chlorine and converted to high boilers; pure 1,2-dichloroethane is distilled off overhead from high boilers, in a second distilling zone; and residual dichloroethane is distilled off under reduced pressure from high boiler concentrate, in a third distilling zone, and the high boilers are removed, which process comprises: introducing high boiler-containing effluent coming from the chlorination of low boiler concentrate into the lower portion of the third distilling zone.

An advantageous embodiment of the present process provides for distillate containing 1,2-dichloroethane coming from the third distilling zone to be recycled to the center portion of the first distilling zone. This step has been found to produce beneficial effects even in those cases in which high boiler-containing effluent coming from the chlorination of low boiler concentrate is recycled, in known manner, approximately to the center portion of the first distilling zone.

EXAMPLE 1

(Comparative Example, FIG. 1)

36,000 kg/h of 1,2-dichloroethane was introduced into a cracking plant and cracked at a rate of about 50.5%. 17,820 kg/h of 1,2-dichloroethane was recovered for purification by distillation. To this end, a partial stream (4) of 400 l/h was taken from the reflux material of low boiler column (2), treated in chlorination container (5) with 20 kg/h of chlorine coming from conduit (6), and recycled to column (2) through conduit (7).

It was possible for the low boiler column (2) to be operated over a period of 65 days and for the associated circulation evaporator (9) to be operated over a period of 215 days.

1,2-dichloroethane with a purity of 98.8% was taken from high boiler column (11) through head conduit (12).

Cokefaction inside the cracking coil resulted in a pressure increase of 45.55 millibars/day.

EXAMPLE 2

(FIG. 2)

The procedure was as in Example 1, but effluent matter (7) coming from the chlorination container (5) was introduced into the lower portion of vacuum column (15).

As a result of this, it was possible for the low boiler column (2) to be operated over a prolonged period of 730 days and for the associated circulation evaporator (9) to be operated over a period of 580 days.

1,2-dichloroethane with a purity of 99.2% was taken from the high boiler column (11) through head conduit (12).

Cokefaction inside the cracking coil resulted in a reduced pressure increase of only 21.15 millibars/day.

EXAMPLE 3

(FIG. 3)

The procedure was as in Example 1, but effluent matter (16) coming from vacuum column (15) was introduced into the center portion of low boiler column (2).

It was possible for the low boiler column (2) and circulation evaporator (9) to be operated over an unchanged period of 730 and 580 days, respectively, 1,2-dichloroethane with a purity of 99.6% was taken from the high boiler column (11) through head conduit (12). Cokefaction inside the cracking coil resulted in a pressure increase of even less than 10.25 millibars/day.

We claim:

1. In a process for purifying 1,2-dichloroethane which is recovered during incomplete thermal cracking to vinyl chloride and contains contaminants boiling at a temperature lower than 83.7° C. under a pressure of 1011 millibars, briefly termed low boilers hereinafter, and contaminants boiling at a temperature higher than 83.7° C. under a pressure of 1011 millibars, briefly termed high boilers hereinafter, wherein the low boilers are distilled off overhead from contaminated 1,2-dichloroethane, in a first distilling zone; a portion of low boiler concentrate is continuously treated at 30° to 85° C. with gaseous chlorine and converted to high boilers; pure 1,2-dichloroethane is distilled off overhead from the high boilers, in a second distilling zone; and residual dichloroethane is distilled off under reduced pressure from high boiler concentrate, in a third distilling zone, and the high boilers are removed, the improvement which comprises: introducing high boiler-containing effluent coming from the chlorination of low boiler concentrate into the lower portion of the third distilling zone.

2. The process as claimed in claim 1, wherein distillate containing 1,2-dichloroethane coming from the third distilling zone is recycled to the center portion of the first distilling zone.

* * * * *